US011116911B2

(12) United States Patent
Wu

(10) Patent No.: US 11,116,911 B2
(45) Date of Patent: Sep. 14, 2021

(54) INJECTOR LOCKOUT PREVENTION DEVICE

(71) Applicant: Biogen MA Inc., Cambridge, MA (US)

(72) Inventor: Haiming Wu, Weston, MA (US)

(73) Assignee: BIOGEN MA, INC., Cambridge, MA (US)

( * ) Notice: Subject to any disclaimer, the term of this patent is extended or adjusted under 35 U.S.C. 154(b) by 10 days.

(21) Appl. No.: 15/484,642

(22) Filed: Apr. 11, 2017

(65) Prior Publication Data
US 2017/0290990 A1 Oct. 12, 2017

Related U.S. Application Data

(60) Provisional application No. 62/321,052, filed on Apr. 11, 2016.

(51) Int. Cl.
*A61M 5/32* (2006.01)
*A61M 5/20* (2006.01)
*A61M 5/315* (2006.01)

(52) U.S. Cl.
CPC ........ *A61M 5/3204* (2013.01); *A61M 5/2033* (2013.01); *A61M 5/31578* (2013.01); *A61M 5/326* (2013.01); *A61M 2005/2073* (2013.01)

(58) Field of Classification Search
CPC ............ A61M 5/2033; A61M 5/31578; A61M 5/3243; A61M 5/3257; A61M 5/3204; A61M 5/326; A61M 2005/2073; A61M 2005/3263; A61M 2005/208; A61M 2005/3267; A61M 2005/2013; A61M 2005/3268; A61M 2005/206; A61M 2005/3261; A61M 2005/3264; A61M 2005/3217; A61M 2005/3254; A61M 5/3273; A61M 5/3275; A61M 5/0637; A61M 5/3245; A61M 5/50; A61M 5/1626; A61M 5/3216; A61M 5/3219; A61M 5/3232; A61M 5/20; A61M 5/3254; A61M 5/3271; A61M 5/3272; A61M 25/0637

See application file for complete search history.

(56) References Cited

U.S. PATENT DOCUMENTS

| | | | |
|---|---|---|---|
| 2008/0147006 A1* | 6/2008 | Brunnberg | A61M 5/2033 604/136 |
| 2013/0204229 A1* | 8/2013 | Olson | A61M 5/50 604/506 |
| 2015/0202373 A1* | 7/2015 | Creaturo | A61M 5/46 604/117 |
| 2017/0007621 A1* | 1/2017 | Wotton | A61K 31/568 |
| 2018/0193562 A1* | 7/2018 | Gibson | A61M 5/20 |

FOREIGN PATENT DOCUMENTS

WO WO-2015197867 A1 * 12/2015 .......... A61M 5/2033

* cited by examiner

*Primary Examiner* — Amber R Stiles
*Assistant Examiner* — Alexandra Lalonde
(74) *Attorney, Agent, or Firm* — Finnegan, Henderson, Farabow, Garrett & Dunner LLP

(57) ABSTRACT

A device that prevents the accidental activation and lockout of an autoinjector. In illustrative embodiments, a resistance unit is configured to resist deployment of the needle until a critical force is applied by the user to the autoinjector, at which point, the resistance of the resistance unit is overcome. Continuous application of force by the user after the resistance is overcome drives the delivery device to the injection site where the medication is administered.

4 Claims, 4 Drawing Sheets

INJECTOR LOCKOUT PREVENTION DEVICE

BACKGROUND

Field

The present disclosure relates to devices and methods of administering, injecting, and/or delivering substances to a patient. More particularly, and without limitation, the disclosed embodiments relate to preventing inadvertent lockout of an autoinjector typically employed in regimented therapies and emergency situations.

Description of Related Prior Art

Autoinjector delivery systems are devices that facilitate hypodermic administration or self-administration of a predetermined dosage of medication. Often times, a patient's therapeutic regimen calls for periodic, for example, daily or weekly administrations of medication using autoinjectors. For example, in the treatment of multiple sclerosis, some patients are prescribed daily injections of disease modifying drugs, such as Interferon beta 1a for the treatment of multiple sclerosis, or, for example, AVONEX® available from Biogen. Auto injectors are also useful in emergency situations. Anaphylaxis, for example, is a serious allergic reaction that occurs rapidly and may cause death. Typically caused by contact with animals, food, and/or medication, common symptoms of anaphylactic shock include an itchy rash, throat swelling, and low blood pressure. In such cases, the immediate administration of epinephrine, antihistamines, and/or steroids is desirable.

Typically, autoinjectors have a syringe or similar structure containing drug substances. The syringe is disposed within a housing and is displaced by a spring when activated, causing a needle to be exposed to an injection site. After the injection occurs and the medication has been expelled from the syringe, a needle guard is deployed to prevent any harm, such as puncture injury and/or contamination, that may otherwise result from an exposed needle. Further, post injection, the needle can assume a lockout condition, wherein the needle is locked into its retracted position and cannot be deployed a second time. The lockout condition can also provide a user with one or more indicators—e.g., visual, tactile, etc.—that indicate whether the single-use autoinjector has already been used, prevents its reuse, and avoids harm that might result from an exposed needle.

An inadvertent lockout problem can arise during use of the autoinjector from hesitation or misapplication. Inadvertent lockout renders the autoinjector useless for its intended purpose as if the medication has been expelled from the single use device. This inadvertent lockout can occur in patients who regularly use autoinjectors, and is not limited to the less practiced environment where the autoinjector is used in emergency situations. The consequences of an inadvertent lockout in an emergency situation can be more dire, however, for example where anaphylaxis is present and time is of the essence.

During an emergency, the stress of the moment can cause anxiety and nervousness in the user, which can affect the user's technique. Likewise, the ability of the person receiving an injection to remain still can be affected. Hesitation and apprehensive fidgeting with the autoinjector is therefore a common result, which often prolongs the time required for successful administration. Additionally, a user's unfamiliarity with an autoinjector can create uncertainty regarding how to activate it, and where on the body to deliver the injection. These factors can increase the chance of injection failure because, as explained above, the autoinjector's lockout mechanism is designed so that the user has only one chance to administer the medication properly.

Under the most unfortunate circumstances, users have been known to accidentally activate the autoinjector prematurely, causing the medication to wastefully dispense and the lockout condition to occur before the autoinjector is securely placed at the injection sight. In other instances, the lockout can be inadvertently activated without dispensing the medication, rendering the medication inaccessible. Inadvertent lockout of the autoinjector under either circumstance renders the medication unavailable for therapeutic use, which renders the autoinjector useless for its intended purpose.

SUMMARY

The disclosed embodiments include devices that prevent the inadvertent lockout of an autoinjector.

In illustrative embodiments, a lockout prevention device is provided for an autoinjector having a housing, a delivery device, and a needle guard. The delivery device contains a syringe or vial filled with a medication for example; it may have a needle located at one end that is enclosed by the needle guard. The needle guard is connected to the delivery device and is configured to retract into the housing so that the needle dispenses medication at an injection site. The lockout prevention device may comprise a resistance unit configured to contact the delivery device in a first position, thereby obstructing the displacement of the needle guard and preventing the delivery device from moving through the housing.

To move the resistance unit from the first position to a second, where the resistance unit no longer obstructs the delivery device from traveling to the injection site, a user must overcome a resistance by applying a critical force to the needle guard. After the resistance is overcome, the needle guard can retract freely into the housing such that application of a lesser, injection force to the needle guard exposes the needle to the injection site where the medication is administered. The lesser, injection force may be achieved from momentum generated by applying the critical force. Therefore, in an exemplary operation, a user must overcome a resistance by applying a critical force to the autoinjector in order to prepare it for injection, and, once overcoming the resistance, provide a lesser force sufficient to make the injection and lockout occur. Accordingly, another aspect of the disclosed embodiments is to assist users in making a proper injection by allowing the them to practice applying an activating force without lockout occurring. This training prevents hesitation, apprehensive fidgeting, and/or misapplication of the autoinjector that might otherwise cause an inadvertent lockout.

According to exemplary embodiments of the current disclosure, a user is required to overcome a resistance at the injection site before the injection occurs in order to better prepare a patient for the impending injection. Overcoming the resistance trains the user to apply a force sufficient to activate the autoinjector without lockout occurring. Beneficial training also results from a user applying a force to the injector that does not exceed the critical force such that the resistance is not yet overcome. The user's mental preparedness is further enhanced because overcoming the resistance builds momentum that carries the user through the injection process with confidence. Therefore, yet another aspect of the disclosed embodiments is to increase the level of a patient's preparedness when using an autoinjector to allow for a proper, confident injection.

Other embodiments of this disclosure are disclosed in the accompanying drawings, description, and claims. Thus, this summary is exemplary only, and is not to be considered restrictive.

BRIEF DESCRIPTION OF DRAWINGS

The accompanying drawings, which are incorporated in and constitute part of this specification, and together with the description, illustrate and serve to explain the principles of various exemplary embodiments.

DETAILED DESCRIPTION OF EXEMPLARY EMBODIMENTS

Figure 1:
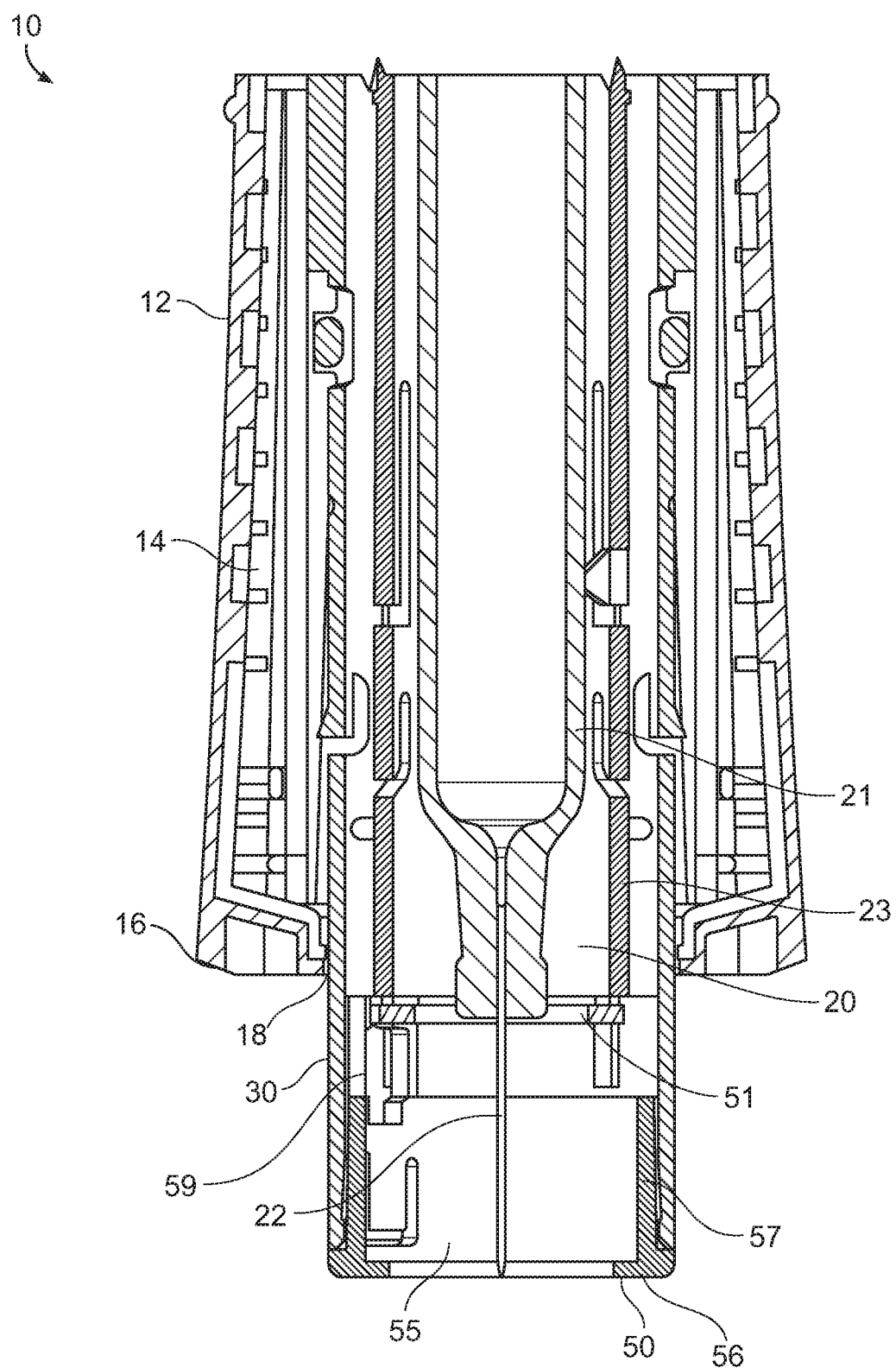
FIG. 1 depicts an exemplary autoinjector device with a resistance unit in a first position according to the present disclosure.
Figure 2:
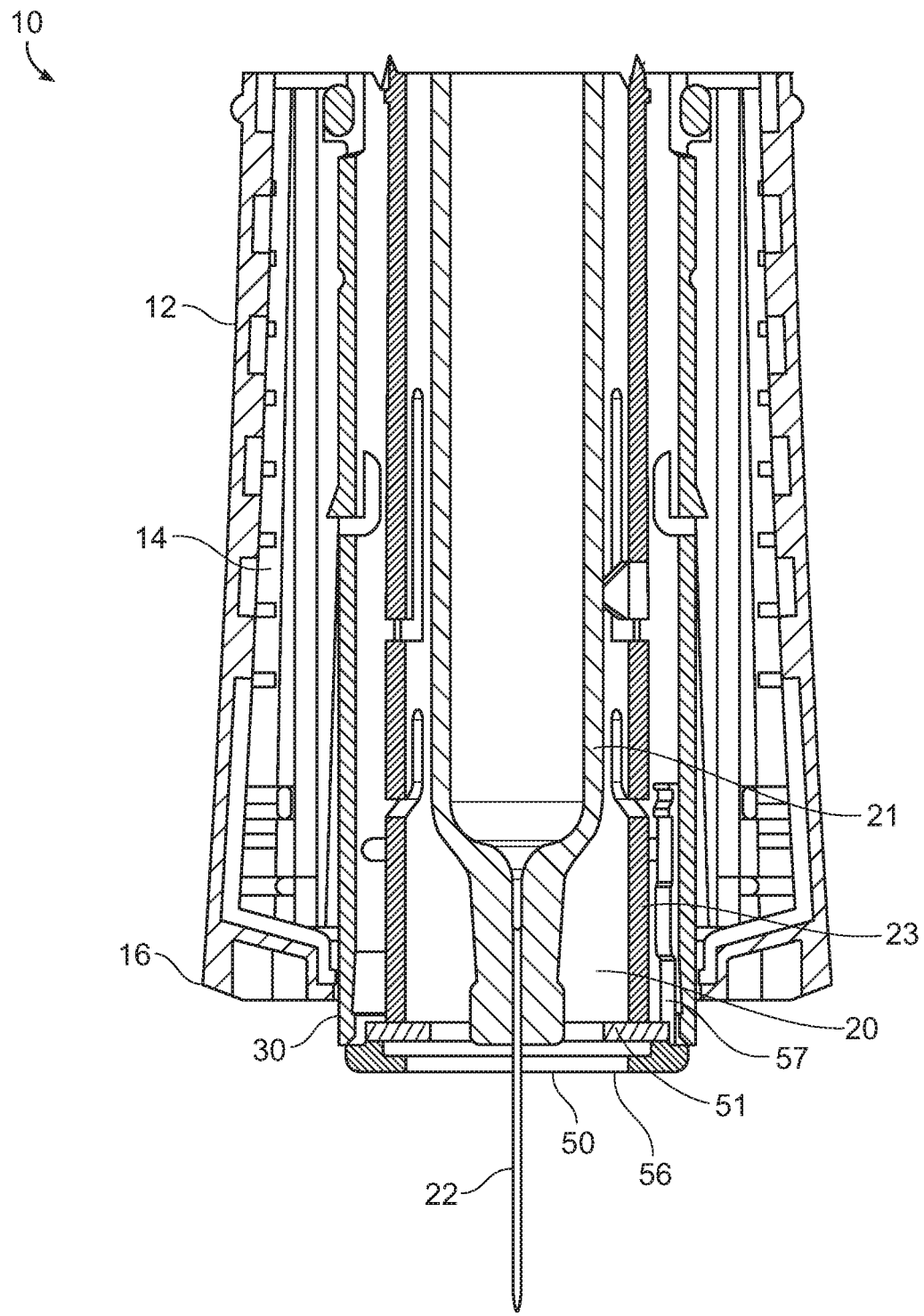
FIG. 2 depicts an exemplary view of the autoinjector of FIG. 1 with the resistance unit in a second position according to the present disclosure.

The claimed subject matter is described with reference to the drawings, wherein like reference numerals are used to refer to like elements throughout. In the following description, for purposes of explanation, numerous specific details are set forth in order to provide a thorough understanding of the subject innovation. It may be evident, however, that the claimed subject matter may be practiced without these specific details. In other instances, well-known structures and devices are shown in block diagram form in order to facilitate describing the subject innovation. Moreover, it is to be appreciated that the drawings may not be to scale. Moreover, the words "exemplary" or "illustrative" are used herein to mean serving as an example, instance, or illustration. Any aspect or design described herein as "exemplary" or "illustrative" is not necessarily to be construed as preferred or advantageous over other aspects or designs.

According to an illustrative embodiment of the disclosure, an autoinjector 10 has a lockout prevention mechanism. In an exemplary embodiment, the autoinjector 10 has a housing 12, a delivery device 20, a needle guard 30, and a resistance unit 50. Preferably, the housing 12 is made from thermoplastic, but any other suitable material can be used in accordance with the present disclosure. The delivery device 20 is preferably made from glass, but, again, any other suitable material can be used in accordance with the present disclosure.

In an exemplary embodiment shown in FIG. 1, the housing 12 includes an elongated body 14 that is hollow. The elongated body 14 has two ends—a closed proximal end (not shown), and an open distal end 16. The open distal end 16 of the housing 12 provides an opening 18 through which the delivery device 20 protrudes. The housing 12 is sufficiently large to allow for enhanced, ergonomic handling. To further enhance the easy of handling, the housing 12 can, for example, have a textured outer surface, ribs disposed thereon, and/or a curved housing. Also, in an exemplary embodiment, the housing 12 is comprised of two or more materials, wherein at least one material has improved gripping qualities over the other(s).

In an exemplary embodiment, the housing 12 has a viewing window (not shown) in the elongated body 14 that allows a user to observe the delivery device 20 disposed therein. The viewing window can comprise an open aperture in a wall of the elongated body of the housing 12, or the open aperture can be covered by a transparent or translucent member. By enabling observation of the viewing window, an additional indicator as to the status of the delivery device 20 is provided. This can be useful to determine whether the delivery device 20 contains contents, determine whether said contents have already been dispensed, and to observe dispensing while it occurs.

FIG. 1 further discloses an exemplary embodiment of the delivery device 20 within the housing 12. The delivery device 20 may comprise a syringe 21 or vial disposed within a holder 23. In some embodiments, the syringe 21 contains a medication, and can also contain other materials, such as, for example, vitamins and/or other therapeutic substances. The holder 23 cooperates with the syringe 21 when the syringe 21 is exposed to an injection site. As discussed in further detail below, FIG. 1 depicts a needle 22 of the syringe 21 disposed within the housing 12 while the resistance unit 50 is in a first position. Because the needle 22 is fully enclosed by the needle guard 30, it avoids contact with contaminating objects or surfaces.

Both the syringe 21 and the holder 23 of the delivery device 20 are connected to a needle guard 30. A portion of the needle guard 30 extends beyond the open distal end 16 of the housing 12. The needle guard 30 encloses the needle 22 attached to the syringe 21 so that a user never has to view the needle. This feature therefore provides a benefit to patients with a phobia of needles. As shown in FIG. 1, the needle guard 30 is can be cylindrically shaped and hollow, so as to surround the delivery device 20, but it should be appreciated that other shapes, in addition to hollow cylinders, are contemplated (e.g., rectangular shaped hollow needle guards). The needle guard 30 is movable within and/or retractable into the housing 12. The needle guard 30 further comprises a spring mechanism (not shown) that is triggered by moving the needle guard 30 towards the closed proximal end of the housing 12. (The internal drive mechanism, including the spring mechanism, of the autoinjector may not be germane to the illustrative embodiments herein disclosed. But the internal drive mechanisms disclosed in U.S. Pat. No. 7,442,185 and U.S. Patent Pub. No. 2014-0309591 are herein incorporated by reference.) Movement of the needle guard 30 beyond a critical point triggers the spring mechanism, which, as stored, contains potential energy. The spring mechanism is connected to a plunger of the syringe 21 so that, when triggered, it moves the plunger, located at least in part inside the delivery device, towards the needle 22 to facilitate dispensing.

After injection and dispensing occur, a portion of the needle guard 30 extends back outside of the housing 12 via a negative spring disposed inside the housing 12 at the open distal end 16 thereof. Also, the needle guard 30 is locked into an extended position such that a portion of the needle guard 30 extends outside of the housing 12 beyond the open distal end 16 thereof. This configuration is known as the lockout condition. The lockout conditions prevents the needle 22 extending beyond the needle guard 30. Further, it allows a user to appreciate that the autoinjector 10 has been used and is ready for disposal.

FIG. 1 further depicts an exemplary embodiment of an assembly of the autoinjector 10 with the resistance unit 50 disposed within a distal end of the needle guard 30 in the first position. The resistance unit 50 comprises a ring 51 and a base 55. The ring 51 is connected to, and movable within, the base 55. In some embodiments, the ring 51 comprises at least two protrusions 52 extending from a perimeter thereof. The protrusions 52 are diametrically opposed to one another. The protrusions 52 are received by arms 59 of the base 55 to secure the resistance unit 50 in the first position. As shown in FIG. 1, when in the first position, the ring 51 abuts an end of the holder 23 of the delivery device 20, thereby preventing: (1) the spring mechanism from triggering; and (2) the delivery device 20 from being exposed to an outside of the housing 12 and to the injection site.

Figure 3:
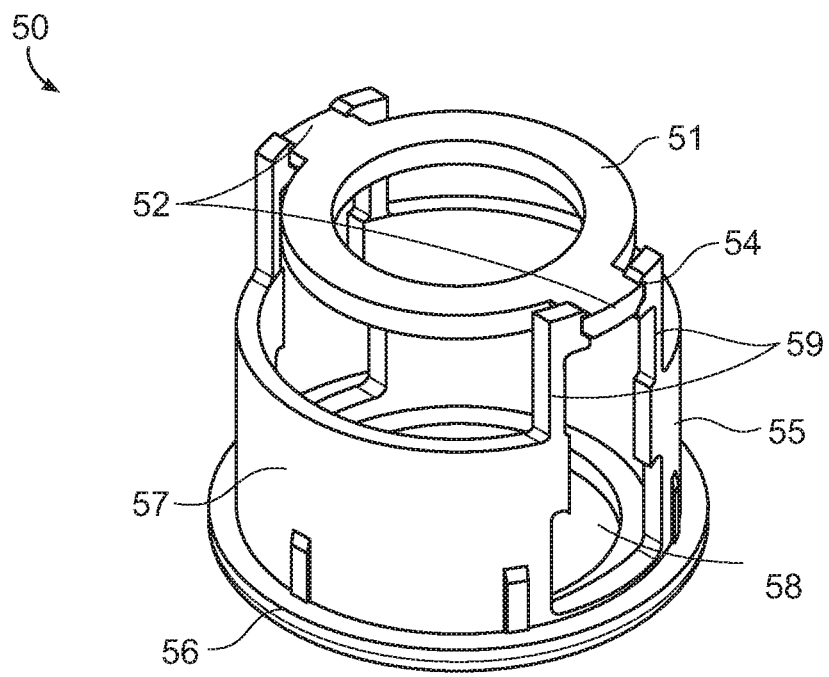
FIG. 3 depicts an exemplary resistance unit in a first position according to the present disclosure.
Figure 4:
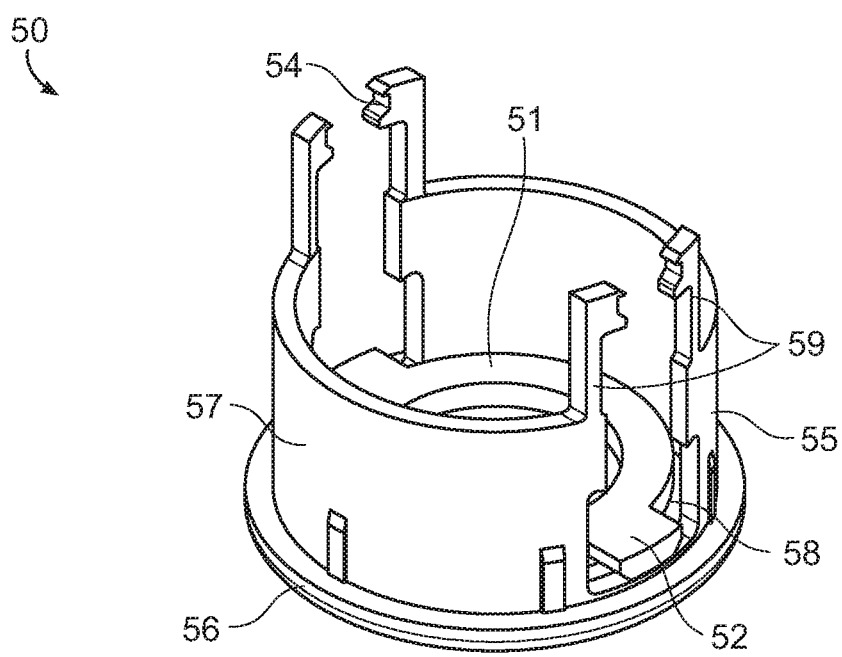
FIG. 4 depicts an exemplary resistance unit of FIG. 3 in a second position according to the present disclosure.
Figure 5:
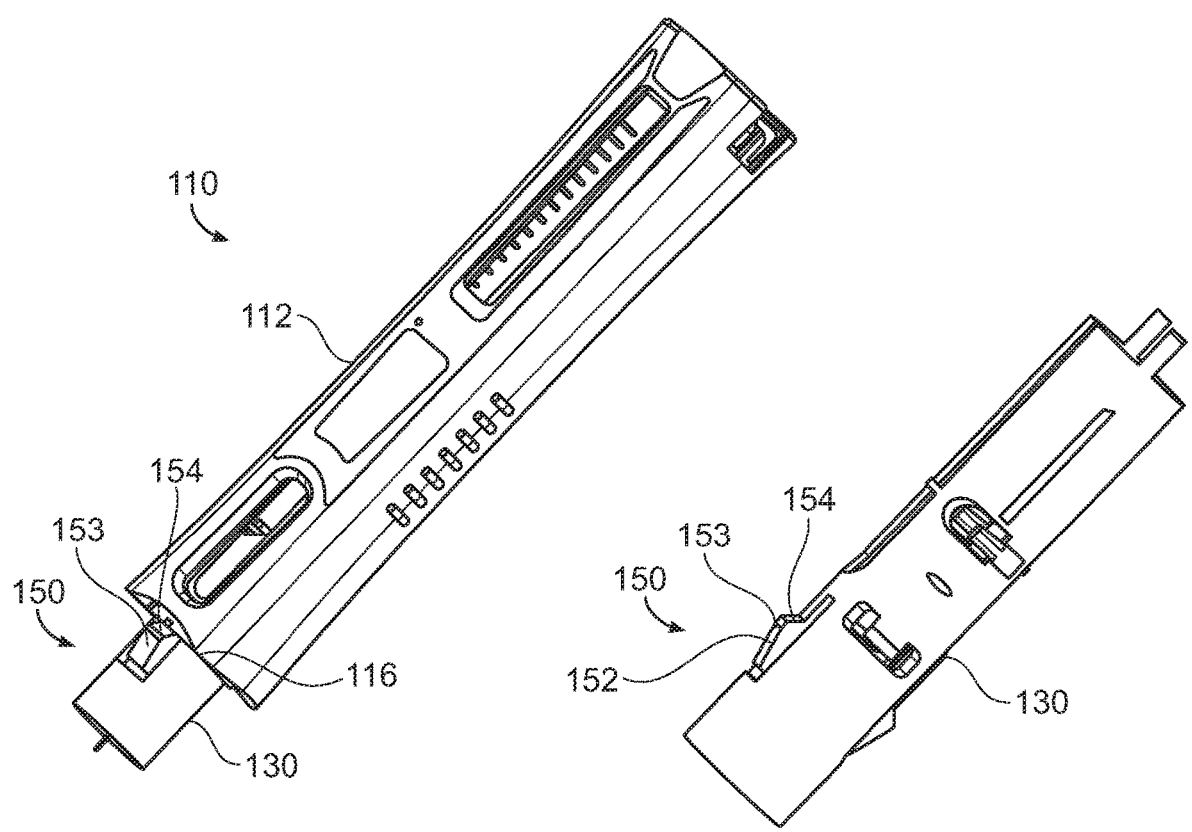
FIG. 5 depicts an alternative exemplary resistance unit according to the present disclosure.

As shown in FIG. 3, the base 55 is comprised of an annular end 56 and a skirt 57 proximally extending away from the annular end 56. In one embodiment, the skirt 57 has a skirt opening 58 for receiving the protrusions 52 of the ring 51. The skirt 57 further has arms 59 proximally extending away from the skirt 57 so as to assume a cantilevered configuration. Distal ends of each arm contain a recess 54 for securely positioning the protrusions 52 of the ring 51 therein. In this way, the ring 51 is secured to the base 55 at a distance away from the annular end 56 when in the first position. Further, as discussed below, because the arms 59 are cantilevered from the skirt 57, applying a critical force to the needle guard 30 will cause the arms 59 to flex outwardly. As a result, the ring 51 will be released from the recess 54 and fall to the annular end 56 of the base 55, as shown in in FIG. 4. The autoinjector 10 is ready for administration only after the critical force is applied to the needle guard 30 to free the ring 51 from the arms 59 of the resistance unit 50. After, a user can apply a lesser injection force to administer the medication contained in the autoinjector 10.

Alternative embodiments of the resistance unit 50 have been contemplated in accordance with the present disclosure. For example, in some embodiments, the resistance unit 50 is formed integrally with the needle guard 30. In another embodiment, the base 55, for example, need not have arms 59 cantilevered from a skirt 57 in order to provide a means for maintaining the ring 51 in the first position. The entire skirt 57, for example, can extend further away from the annular end 56 and provide a recess 54 for receiving the protrusions 52 of the ring 51. So long as the resistance unit 50 obstructs the needle guard 30 from retracting into the housing 12, the resistance unit 50 can assume any configuration.

For example, in another embodiment, the ring 51 shown in FIG. 1 that abuts a distal end of the holder 23 need not be a ring at all; rather, it could assume different shapes, such as, for example, an arcuate shape or a straight bar with a hole in its center to accommodate the needle 21.

In another embodiment, there is no ring 51; instead, at least one arm extends away from the annular end 56 of the base 55 and abuts the distal end of the holder 23 to prevent movement of the needle guard 30 towards the closed proximal end of the housing. Distal ends of the at least one arm may have a chamfered surface or detent extending therefrom that cooperates with the distal end of the holder 23, such that when a force applied to the needle guard 30 exceeds a critical point, the arm flexes and is freed from the holder 23, allowing the injection process to proceed.

In other embodiments, the resistance unit 50 comprises at least one arm that has a frangible portion that is disposed within the needle guard 30 and abuts the distal end of the holder 23. During use, the frangible portion can collapse in response to a critical force being applied to the needle guard 30, thereby allowing the needle guard to move towards the closed proximal end of the housing 12 to trigger the spring mechanism.

In another embodiment, an autoinjector 110 has a resistance unit 150 that is integral with a needle guard 130. The resistance unit 150 can comprise at least one cantilevered spring 152 that is attached to the body of the needle guard 130 on one end, and has a protrusion 153 extending from another, distal end thereof. The protrusion has a ramped surface 154 that abuts an open distal end 116 of the housing 112. In use, as a user presses down on the autoinjector 110 at the injection site, the needle guard 150 is moved towards the closed proximal end of the autoinjector. As the force applied to the needle guard 130 increases, the open distal end 116 of the housing 112 travels along the ramped surface 154 of the cantilevered spring 152, moving the cantilevered spring towards an interior of the needle guard 130. When the force applied exceeds a critical force, the needle guard 130 can move freely through the housing 112 to trigger the spring mechanism (not shown), causing the injection to occur.

According to the exemplary embodiment of the present disclosure, the autoinjector 10 can also include a removable end cap (not shown) that encloses the open distal end 16 of the housing 12, including the delivery device 20, needle guard 30, and resistance unit 50. The closure protects critical features of the autoinjector 10 against harm during transport and storage. The end cap is selectively removable when the autoinjector 10 is ready for use. Also, the end cap can be re-applied to the autoinjector 10 thereafter to further prevent contact with the needle 22. In some embodiments, the end cap has a ribbed or textured outer surface, which may comprise a different material than other portions of the autoinjector, for enhanced gripping and handling.

In operation, the removable end cap is removed from autoinjector 10 to reveal the needle guard 30 and the resistance unit 50 in the first position, as depicted by the exemplary embodiment in FIG. 1. A user will then position the autoinjector 10 at the injection site. While in the first position, the ring 51 of the resistance unit 50 abuts or is immediately adjacent to a distal end of the holder 23. The user will then apply a critical force by pressing the autoinjector 10 against the injection site. Application of the force to the needle guard 30 urges it towards the closed proximal end of the housing 12. A slight displacement of the needle guard 30 towards the closed proximal end of the housing 12 causes the ring 51 to contact an end of the holder 23, and opposing forces to be applied to the ring 51 and arms 59 of the resistance unit 50. As the force applied exceeds a predetermined criticality and the arms 59 flex outwardly, the ring 51 is released from them, allowing the resistance unit 50 to move into a second position wherein the ring 51 rests against the annular end 56 of the base 55. At which point, the autoinjector 10 is ready for injection.

However, prior to exceeding the critical force required to free the ring 51 from the arms 59, a user could, optionally, repeatedly approach the criticality by asserting a lesser force to the needle guard 50 without risking inadvertent lockout because the arms 59 are designed to provide enough resistance to allow a user to practice before injecting the needle 21. In some embodiments, the critical force required to overcome the resistance caused by the resistance unit 50 can be substantially between five and ten pounds.

After exceeding the critical force, the confidence of the user is advantageously buoyed because he or she is better prepared mentally for the impending injection. A user can then apply a lesser, injection force to the needle guard 30

(which generally results from momentum caused by application of the critical force) continuously pressing the needle guard 30 against the injection site to move the needle guard 30 towards the closed proximal end of the housing 12. Displacement of the needle guard 30 beyond a critical point triggers the spring mechanism, which exposes the syringe 22 and drives the plunger of the delivery device 20 to the injection site, thereby dispensing the medication.

By this exemplary administration process, a user may avoid hesitating or fidgeting with the autoinjector 10, thereby preventing an inadvertent lockout and the associated consequences discussed above. Further, the user's preparedness is enhanced because overcoming the resistance of the resistance unit 50 builds momentum that carries the user through the injection process with confidence.

While the foregoing drawings and descriptions set forth functional aspects of the disclosed systems, no particular arrangement of these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

Further, while embodiments of the present disclosure have been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

What is claimed is:

1. An autoinjector, comprising:
    a housing having a proximal end and a distal end;
    a delivery device disposed within, and moveable relative to, the housing, wherein the delivery device comprises a syringe;
    a needle guard at the distal end of the housing, the needle guard being coupled to the syringe and configured to move the syringe through the housing to an injection site; and
    a resistance unit having a proximal end and a distal end, the entire proximal end of the resistance unit being disposed within the needle guard,
    the resistance unit comprising a ring and a base;
        the ring comprising at least one protrusion; and
        the base comprising an annular end wall, a skirt extending from the annular end wall, and cantilever arms extending from the skirt, the cantilever arms comprising at least one recess configured to receive the at least one protrusion; and
    the resistance unit being configured to have a first position, wherein the cantilevered arms receive the at least one protrusion such that the resistance unit prevents the needle guard from exposing the syringe to the injection site, and a second position, wherein the resistance unit does not prevent the needle guard from exposing the syringe to the injection site;
    wherein an injection force, required to expose the syringe to the injection site, is transmitted by application of a critical force to the autoinjector, which is required to move the resistance unit from the first position to the second position.

2. The autoinjector of claim 1, wherein movement of the resistance unit from the first position into the second position, by applying a critical force to the autoinjector, is configured to release the at least one protrusion from the cantilevered arms.

3. The autoinjector of claim 1, wherein, in the second position, application of the injection force to the autoinjector is configured to cause the needle guard to expose the syringe to the injection site; and wherein the injection force is less than the critical force.

4. The autoinjector of claim 1, wherein the autoinjector further comprises an end cap for selectively covering the distal end of the housing and the needle guard.

* * * * *